US006730041B2

(12) United States Patent
Dietrich

(10) Patent No.: US 6,730,041 B2
(45) Date of Patent: *May 4, 2004

(54) LEARNING DISABILITIES DIAGNOSTIC SYSTEM

(76) Inventor: Diane Dietrich, 7 Carmel Ct., Old Bridge, NJ (US) 08857

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 30 days.

(21) Appl. No.: 09/837,287

(22) Filed: Apr. 18, 2001

(65) Prior Publication Data

US 2003/0088159 A1 May 8, 2003

(51) Int. Cl.$^7$ ................................................ A61B 5/00
(52) U.S. Cl. ...................... 600/558; 600/301; 600/559; 128/920; 128/904; 434/178
(58) Field of Search ................... 600/300–301, 600/558–559; 128/904, 920–925; 434/262, 236, 118, 178, 159, 167, 184, 185; 704/1, 200, 246

(56) References Cited

U.S. PATENT DOCUMENTS

| 5,381,805 A | * | 1/1995 | Tuckett et al. ............... 600/555 |
| 5,711,671 A | * | 1/1998 | Geeslin et al. ............... 434/236 |
| 5,868,683 A | * | 2/1999 | Protopapas et al. ......... 600/559 |
| 5,927,988 A | * | 7/1999 | Jenkins et al. ............... 434/116 |
| 6,045,515 A | * | 4/2000 | Lawton ........................ 600/558 |
| 6,075,968 A | * | 6/2000 | Morris et al. ................ 434/350 |
| 6,146,147 A | * | 11/2000 | Wasowicz .................... 434/169 |
| 6,234,965 B1 | * | 5/2001 | Miller et al. ................. 600/300 |
| 6,299,452 B1 | * | 10/2001 | Wasowicz et al. ........... 434/178 |
| 6,398,729 B1 | * | 6/2002 | Levinson ..................... 600/300 |

OTHER PUBLICATIONS

Keith E. Beery, Ph.D. and Norman A. Buktenica, VMI—The Beery–Buktenica Developmental Test for Visual–Motor Intregation, 4th Ed.

* cited by examiner

Primary Examiner—Max F. Hindenburg
Assistant Examiner—Michael Astorino
(74) Attorney, Agent, or Firm—Mathews, Collins, Shepherd & McKay, P.A.

(57) ABSTRACT

The present invention relates to a learning disabilities diagnostic system in which a remote station includes a visual assessment component and an auditory assessment component. A diagnostic station is coupled by a communication interface to the remote station. The diagnostic station receives the visual assessment component and auditory assessment component and prepares an assessment based on the information received. Accordingly, the diagnostic system allows a user to complete visual assessment tests and auditory assessment tests in their own environment for prescreening of learning disabilities.

6 Claims, 1 Drawing Sheet

LEARNING DISABILITIES DIAGNOSTIC SYSTEM

BACKGROUND OF THE INVENTION

1. Field of the Invention

The present invention relates to a learning disabilities diagnostic system in which a remote visual assessment component and an auditory assessment component are forwarded to the system and the system prepares an assessment based on the visual assessment component and auditory assessment component.

2. Description of Related Art

Nearly 20% (1 in 5) of the nation's children between the ages of 5 and 12 may be challenged by one or more learning disabilities. This is an astonishingly large number of children, vastly beyond the capabilities and resources of most school systems to properly identify learning disabilities or to adequately provide for them. Many teachers, already burdened by classroom overcrowding and sheer class size, are simply unable to offer the time and attention required to help these children when they need it most, i.e., while they are still young enough to be aided without stigma or social labeling. Accordingly, it is desirable for parents to have options to test for learning disabilities outside of the school system.

Conventionally trained medical personnel have performed tests at their offices to assess children with learning disabilities. However, the provided medical tests can be expensive and the children are often uncomfortable in the medical surroundings leading to impaired performance on the tests. It is desirable to provide an easily-administerable remote testing environment to inexpensively provide pre-screening of learning disabilities.

SUMMARY OF THE INVENTION

The present invention relates to a learning disabilities diagnostic system in which a remote station includes a visual assessment component and an auditory assessment component. A diagnostic station is coupled by a communication interface to the remote station. The diagnostic system receives the visual assessment component and auditory assessment component and prepares an assessment based on the information received. Accordingly, the diagnostic system allows a user to complete visual assessment tests and auditory assessment tests in their own environment for prescreening of learning disabilities. The invention will be more fully described by reference to the following drawings.

DETAILED DESCRIPTION

Figure 1:
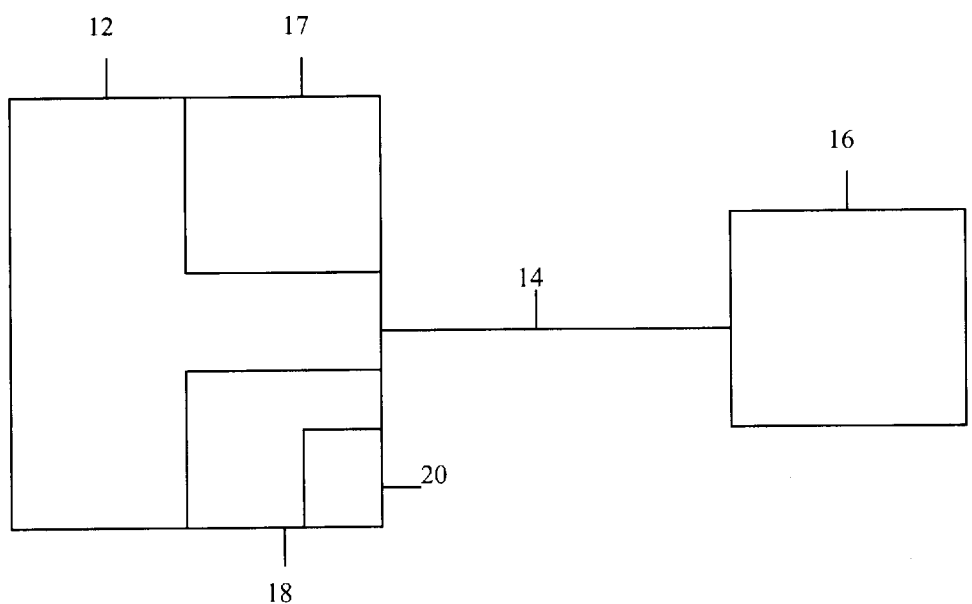
FIG. 1 is a schematic diagram of a learning disabilities diagnostic system in accordance with the teachings of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 illustrates a schematic diagram of a learning disabilities diagnostic system 10 in accordance with the teachings of the present invention. Remote station 12 is coupled through communication interface 14 to diagnostic station 16. For example, remote station 12 can be located at a home of the test subject or a classroom of the test subject and diagnostic station 16 can be located at a medical specialist's office.

Remote station 12 can comprise visual assessment component 17 and auditory assessment component 18. Communication interface 14 can include a connection for visual assessment component 17 and a connection for auditory assessment component 18. For example, diagnostic station 16 can be accessed as a Website and communication interface 14 can comprise an Internet connection for establishing a communication path between remote station 12 and a Web site for diagnostic station 16. Alternatively, communication interface 14 can be a postal mail connection or telephone connection.

Visual assessment component 17 provides testing of visual motor skills. For example, visual assessment component can include diagnostic tests which provide information for evaluating learning disabilities in visual components. An implementation of visual assessment component 17 can include pen and paper tests in which a user completes the test by writing in answers to questions or preparing drawings. The pen and paper tests can be scanned by a conventional scanner to represent the data in electronic form. Alternatively, tests for visual assessment can be provided as a template on a user's computer which is completed by a user or a parent of the user using a keyboard and a mouse interface to the computer.

Tests for visual assessment component 17 are forwarded over communication interface 14 to diagnostic system 16 for evaluation. For example, if remote station 12 includes a personal computer, data from tests of visual assessment component 17 can be electronically forwarded from diagnostic station 16 such as over the Internet or a dial up modem connection. In the alternative, data from tests for visual assessment component 17 can be forwarded by postal mail from remote station 12 to diagnostic station 16. If remote station 12 includes a scanner or fax device, scanned test responses, drawing responses and the like forming electronic data can be electronically forwarded from remote station 12 to diagnostic system 16.

An implementation of auditory assessment component 18 can include an interactive voice response (IVR) system 20. Communication interface 14 further comprises a telephone communications network to connect auditory assessment component 18 to diagnostic station 16. IVR system 20 can record auditory responses at the IVR system 20 such that a user of diagnostic station 16 can later retrieve the auditory responses for evaluation by establishing a telephone connection to IVR system 20. Alternatively, communication interface 14 can also comprise an Internet connection between auditory assessment component 17 and a Web site of diagnostic system 16. IVR system 20 can store the auditory responses as a WAV or similar sound file at the Web site of diagnostic station 16 such that a user of diagnostic station 16 can later retrieve the stored auditory responses over the Internet. Auditory assessment component 18 can provide, for example, testing of auditory discrimination and auditory memory for evaluating learning disabilities in auditory components.

Diagnostic station 16 uses evaluation of the tests from visual assessment component 17 and audio assessment component 18 to provide an assessment of potential learning disabilities of the test subject. For example, diagnostic station 16 can include a computer for automatically evaluating test responses or a medical specialist's review of test responses. A report outlining the assessment can be generated by diagnostic station 16. The report can be forwarded by email or postal mail to remote station 12.

In general, system 10 provides a low-cost, pre-screening assessment for identifying possible Learning Disabilities (LD) in children ages 5 and older. It is designed to be done by the child with parental assistance in the convenience and privacy of home, and consists of a combination of print materials delivered either via the internet or postal mail, and an Interactive Voice Response (IVR) system that one connects to by phone.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

I claim:

1. A method for providing a prescreening assessment for identifying possible learning disabilities comprising the steps of:

providing a remote station;

determining a visual assessment component and an auditory assessment component at said remote station, said visual assessment component providing testing of visual motor skills for evaluating learning disabilities in visual components and said auditory assessment component providing testing of auditory skills for evaluating learning disabilities in auditory components, said visual assessment component comprises writing answers to questions or preparing drawings, said auditory assessment component comprises one or more tests selected from the group consisting of testing auditory discrimination and testing of auditory memory and recording auditory responses of said one or more tests;

communicating first information of said visual assessment component and second information of said auditory assessment component to a diagnostic station, said auditory assessment component being communicated by retrieving said auditory responses; and preparing at said diagnostic station an assessment of learning disabilities based on said first information and said second information.

2. The method of claim 1 wherein said remote station includes a computer and said visual assessment component includes a test represented by a template on said computer.

3. The method of claim 2 wherein said communicating step is performed by an Internet connection between said remote station and said diagnostic station.

4. The method of claim 1 wherein said auditory assessment component includes an interactive voice response system.

5. The method of claim 3 wherein said communicating step is performed by an Internet connection between said auditory assessment component and said diagnostic station.

6. The method of claim 1 further comprising the step of:

generating a report of said assessment.

* * * * *